Figure 1:
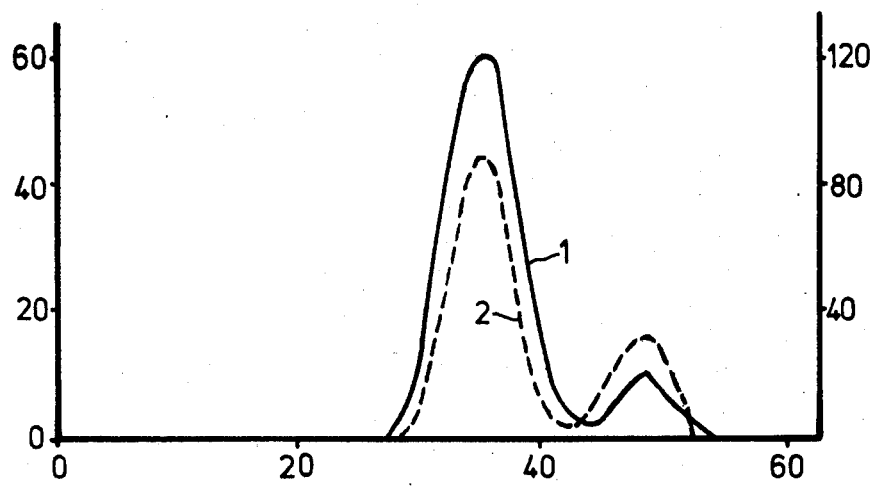

United States Patent [19]

Hochstrasser et al.

[11] Patent Number: 4,485,100

[45] Date of Patent: Nov. 27, 1984

[54] ELASTASE INHIBITORS, A PROCESS FOR THEIR PREPARATION AND MEDICAMENTS CONTAINING THESE INHIBITORS

[75] Inventors: Karl Hochstrasser, Seefeld-Oberalting; Elmar Wachter, Munich, both of Fed. Rep. of Germany

[73] Assignee: Bayer Aktiengesellschaft, Leverkusen, Fed. Rep. of Germany

[21] Appl. No.: 514,033

[22] Filed: Jul. 22, 1983

[30] Foreign Application Priority Data

Aug. 14, 1982 [DE] Fed. Rep. of Germany ....... 3230275

[51] Int. Cl.[3] .................... A61K 37/00; C07C 103/52
[52] U.S. Cl. .............................. 424/177; 260/112.5 R

[58] Field of Search ................. 424/177; 260/112.5 R

[56] References Cited

PUBLICATIONS

I. Schechter, et al., Biochem. and Biophys. Res. Commun., vol. 27, (1967), 157–162.

*Primary Examiner*—Delbert R. Phillips
*Attorney, Agent, or Firm*—Sprung, Horn, Kramer & Woods

[57] ABSTRACT

The invention relates to elastase inhibitors from bovine serum identified herein as BI-I-E and BI-I-E+. Said inhibitors are peptides of the specified amino acid sequence defined herein and they are useful, inter alia, for the treatment of shock, rheumatoid arthritis or pulmonary emphysemia.

9 Claims, 3 Drawing Figures

ELASTASE INHIBITORS, A PROCESS FOR THEIR PREPARATION AND MEDICAMENTS CONTAINING THESE INHIBITORS

The present invention relates to new inhibitors from bovine serum for pancreas and leucocyte elastase, called BI-8-E and BI-8-E+ (bovine inhibitors with Mr 8000 for elastase) below, and to a process for their preparation and medicaments containing these inhibitors.

The elastase inhibitor BI-8-E according to the invention is liberated, together with a structurally homologous trypsin-chymotrypsin inhibitor, called BI-8-T (bovine inhibitor with Mr 8000 for trypsin) below, from the inter-α-trypsin inhibitor, abbreviated to ITI, of cattle by one or more enzymatic reaction steps, and is prepared in a pure form by chromatographic methods. BI-8-E is a glycoprotein in which a carbohydrate moiety built up from residues of N-acetylneuraminic acid, N-acetylglucosamine, galactose and mannose is bonded N-glycosidically via the side-chain of the Asn—in position 24 of the peptide chain. By splitting off the glycoside residue by methods which are known from the literature, a modified inhibitor according to the invention, called Bi-8-E+ in the following text, is obtained from the BI-8-E. Both the inhibitors BI-8-E and BI-8-E+ have identical inhibition spectra, as can be seen from Table 1. Bi-8-E+ has the following structure:

Lys-Ala-Asp-Ser-Cys-Gln-Leu-Asp-Tyr-Ser-Gln-Gly-Pro-Cys-Leu-Gly-Leu-Phe-Lys-Arg-Tyr-Phe-Tyr-Asn-Gly-Thr-Ser-Met-Ala-Cys-Glu-Thr-Phe-Leu-Tyr-Gly-Gly-Cys-Met-Gly-Asn-Leu-Asn-Asn-Phe-Leu-Ser-Gln-Lys-Glu-Cys-Leu-Glu-Thr-Cys-Arg.

This structure is very similar to that of BPTI (basic pancreatic trypsin inhibitor, Kunitz inhibitor) from bovine organs, with a Lysine residue in the active site position 15 or $P_1$ according to the nomenclature of Schechter and Berger [I. Schechter and A. Berger, Biochem. Biophys. Res. Commun. 27, 157–162(1967)], and the inhibitor is therefore called an inhibitor of the Kunitz type.

The aminoacid residue in position 15 or $P_1$ which determines the specificity of the Kunitz inhibitors according to the invention is leucine. The inhibitors are potent inhibitors of pancreatic and leucocyte elastase, chymotrypsin and cathepsin G. They can therefore be used, according to the invention, as medicaments for the therapy of diseases which are caused either by overproduction of these proteinases as a result of increased release from the zymogens or of release during cytolysis, or by a deficit or absence of natural endogenous inhibitors of the enzymes in the organs and tissue fluids. Diseases having this type of etiology are the various forms of shock, post-traumatic or post-operative complications, blood coagulation disorders, acute and chronic inflammatory reactions, and in particular also chronic inflammatory reactions with necrotic and degenerative damage to connective tissue, such as pancreatitis, and immune complex-induced vasculitis, glomerulonephritis, rheumatoid arthritis and other collagenoses, as well as arthritis caused by deposits resulting from metabolism (gout), and also degenerative changes in the elastic elements of vessel walls (atherosclerosis) or of the lungs (pulmonary emphysema).

It has already been disclosed that BPTI [H. Kraut, E. K. Frey and E. Werle, Z. Physiol. Chem. 189, 97 (1930)], also called Kunitz inhibitor [M. Kunitz and H. H. Northrop, J. Gen. Physiol. 19, 991 (1936)], inhibits a number of physiologically important enzymes, such as, for example, kininogenins (kininogenases), plasmin, chymotrypsin and trypsin [E. Werle in W. Brendel and G. Haberland: Neue Aspekte der Trasylol-Therapie (New Aspects of Trasylol Therapy) 5, 9, F. K. Schattauer-Verlag Stuttgart—New York 1972; and H. Fritz, H. Tschesche, L. J. Greene and E. Truscheit (Editors): Proteinase Inhibitors (Bayer Symposium V), Proc. 2nd International Research Conference, Springer-Verlag Berlin-Heidelberg-New York 1974], and is used, as aprotinin (generic name), for the therapy and prophylaxis of shock conditions and for the prophylaxis of post-operative and post-traumatic complications.

It is also known that acid-stable, physiological ITI with Mr 30,000, called BI-30 in the following text, is obtained by deproteinisation of bovine serum with perchloric acid in a manner analogous to that for the deproteinisation of human serum [E. Wachter, K. Deppner, K. Hochstrasser, K. Lempart and R. Geiger, FEBS Letters (1980) 119, 58–62]. However, in contrast to the human system, the supernatant perchloric acid contains another trypsin inhibitor with Mr 8,000, which also inhibits other proteinases, but not elastases, and likewise belongs to the class of Kunitz inhibitors. It does not originate from ITI, and is called BI-8+ in the following text.

It is furthermore known that other inhibitors of the Kunitz type which, as in the human system, originate from ITI are liberated from the perchloric acid precipitate by partial enzymatic hydrolysis with excess proteinases, such as trypsin, plasmin, elastase or kallikrein, in weakly alkaline solution, as described for the human system by Hochstrasser and co-workers [K. Hochstrasser, G. Bretzel, H. Feuth, W. Hilla and K. Lempart, H.S. Z. Physiol. Chem. 357, 153–162 (1976)].

As is known from the human system [E. Wachter, K. Hochstrasser, G. Bretzel and S. Heindl, H.S. Z. Physiol. Chem. 360, 1297–1303 (1979)], this limited proteolysis yields a polyvalent inhibitor with Mr 14,000, called BI-14, in which two inhibitors of the Kunitz type having different specificities are covalently linked via an Arg-Thr bond.

It has now been found that this Arg-Thr bond can be selectively split, by prolonged treatment of the BI-14 with proteinases in weakly alkaline solution, such that the complete inhibitory action of both domains is retained.

According to the invention, proteinases which are suitable for this proteolysis are kallikreins from urine or the pancreas, plasmin and, in particular, trypsin, but also proteinases from plants, fungi or bacteria. The proteinases can advantageously be used in immobilized form, bonded to solid, inert carriers. If immobilized trypsin, preferably trypsin-sepharose, is used, it is advantageous to add the soluble enzyme. Bonding of the anti-tryptically active BI-14 to the trypsin-sepharose is complete even from dilute solutions, and proteolysis with excess bonded or added soluble trypsin proceeds on the carrier, and only those inhibitors which do not inhibit trypsin pass into the supernatant solution.

A molar excess, based on the inhibitors, of the proteinases, especially of those which are inhibited by BI-14, is used for the splitting. This excess can be 10–400%; it is preferably between 150 and 300%. The reactions are carried out in buffered solutions with pH values of 6.5–10, in particular 7.5–8.5. Suitable buffers are prepared using tris-(hydroxymethyl)-aminomethane, triethanolamine, alkali metal borates or phosphates or alkali metal carbonates. If appropriate, the buffers can also contain organic solvents, such as dimethylformamide, dimethylsulphoxide or hexamethylphosphoric acid triamide, and/or salts as additives. The temperature of the reaction mixtures is preferably kept at 37° C. during the proteolysis. However, the splitting can also be carried out at lower or higher temperatures. The reaction time is 1–24 hours, preferably 1–10 hours. The splitting does not proceed to completion. In addition to unreacted BI-14, the reaction mixture contains the two products of hydrolysis BI-8-T and BI-8-E and another elastase-chymotrypsin inhibitor of Mr 14,000, in which the anti-tryptic center is evidently modified and which is called BI-14+ in the following text.

The preferred starting material for obtaining the elastase inhibitor BI-8-E according to the invention is the tandem Kunitz inhibitor BI-14 from bovine ITI. As already mentioned, this acid-stable, polyvalent inhibitor is obtained by limited proteolysis of the precipitate obtained during deproteinisation. As already known, relatively small amounts of BI-14 and its intermediate BI-30 can additionally be isolated from the supernatant of the perchloric acid precipitation [E. Wachter, K. Deppner, K. Hochstrasser, K. Lempart and R. Geiger, FEBS Letters (1980) 119, 58–62].

According to the invention, BI-8-E can also be obtained starting from BI-30 by complete proteolysis using the enzymes already listed, but especially trypsin. It is also possible to use the mixture of BI-14 and BI-30, or the bovine serum itself. In the latter case, a considerably larger amount of enzyme is of course necessary for the splitting, since the acid-labile inhibitors must also first be neutralised or complexed. Thus, in all cases, the desired BI-8-E must be separated off from the contaminating substances having no inhibitory action and the substances having an inhibitory action, such as BI-14, BI-14+, BI-8-T and, if bovine serum, or the inhibitor fraction obtained during deproteinisation or crude BI-14 which has been obtained via reversible complexing with a support carrying immobilized trypsin is used, also BI-8+. FIG. 1 shows the elution profile of a BI-14 trypsinolysis batch on a Sephadex G-75 ® column—column dimensions 3×200 cm; eluting agent 0.05M borate buffer of pH 8.0, 0.2M with respect to sodium chloride; fractions of 24 ml were collected. The numbers of the fractions are shown on the abscissa, and the ordinate shows the antitryptic activity of the eluates on the left and their anti-elastase activity on the right. The data for the inhibition of trypsin or elastase are in milli-inhibitor units/ml of eluate—mIU/ml. The inhibition of the trypsin was determined as described under 2.d., and the inhibition of pig pancreatic elastase was determined as described under 2.a. Curve 1 passing through the circles is for the inhibition of elastase, whilst curve 2 corresponds to the inhibition of trypsin.

Complexing with immobilized trypsin is particularly suitable for separating off the substances having an inhibitory action on trypsin. For this, the enzyme used for the splitting is first preferably removed by precipitation with perchloric acid and centrifugation or filtration. After neutralization and adjustment to a pH value of between 7.5 and 10, the solution containing the inhibitors is mixed with the trypsin-charged carrier or filtered over this support.

BI-8-E does not complex with the trypsin, and BI-14+ has only a slight affinity for trypsin. Both are obtained in the neutral eluates or in the filtrate during rinsing. BI-14+ and BI-8-E are preferably separated by filtering the mixture over a molecular sieve column. Suitable molecular sieves are crosslinked dextrans, such as Sephadex G-50 ®, Sephadex G-75 ® or Sephadex G-100 ®, Bio-Gel P-30 ®, Bio-Gel P-60 ® or Bio-Gel P-100 ®. Particularly suitable solvents for the gel filtration are highly volatile dilute acids, such as acetic acid, or volatile buffers or salt solutions, such as ammonium formiate solutions, ammonium bicarbonate solutions or ammonium acetate solutions. For further purification of BI-8-E, the inhibitor is adsorbed onto a carrier with immobilized chymotrypsin, preferably onto α-chymotrypsin-sepharose, from neutral or weakly alkaline solution, complexing is taking place. After the impurities have been washed out, the complex is dissociated by treatment of the affinity carrier with acid buffers in a manner which is in itself known, in a batch or in a column, the inhibitor being liberated. If dissociation of the complex is carried out in a column, elution can be effected in a relatively small volume. Further concentration can be effected by ultrafiltration, the salts being removed at the same time. However, it is also possible to separate the salts by gel filtration of the concentrate over molecular sieve columns in the manner described above.

Alternatively, the BI-8-E can also be purified by adsorption onto Concanavalin-A-sepharose ®. Before desorption with a solution of α-methylglycoside or α-methylmannoside, the impurities are washed out with water and/or buffer solutions. After removal of the salts by ultrafiltration with an Amicon UM-2 membrane or filtration over a molecular sieve column, the BI-8-E thus obtained can be isolated by freeze-drying.

To isolate BI-8-E, it is particularly advantageous to incubate the neutral eluates or the filtrate from the trypsin column, which contain BI-14+ and BI-8-E, with a carrier with immobilized chymotrypsin, without further manipulations. Complexing of the inhibitor with the immobilized enzyme can be carried out in a batch or by filtration over a column filled with the affinity carrier, bonding being effected from neutral or weakly alkaline solution.

Figure 2:
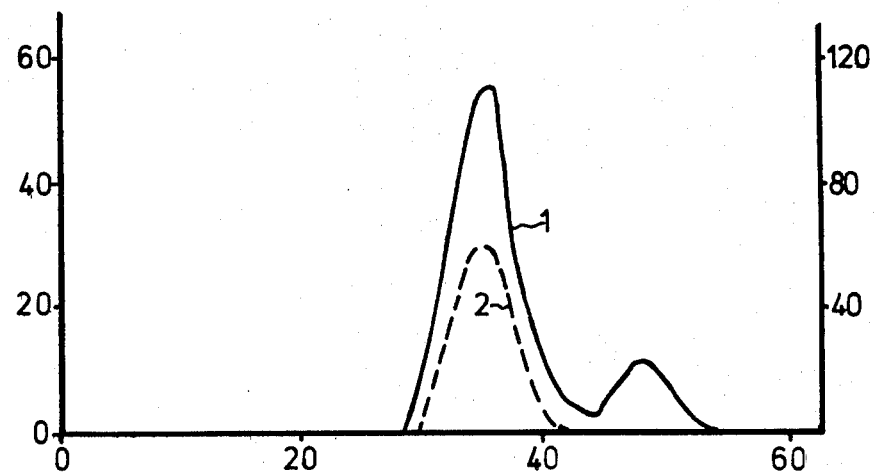

After the impurities have been washed out, the inhibitors are liberated from the complexes by acidification with dilute acids in solutions which preferably contain salts. Particularly suitable acids are hydrochloric acid or formic acid and acetic acid. Sodium chloride or potassium chloride are preferably used as the salts, but other inorganic salts and denaturing agents, such as lithium chloride, guanidinium chloride or urea, are also suitable. The liberation can be carried out either in a batch or in a column. Finally, after neutralization and concentration, the BI-8-E is isolated by gel filtration over suitable molecular sieves, which have already been listed, using the eluting agents which have also already been mentioned. In this method, the salts are removed at the same time. As mentioned several times, the BI-8-E can be isolated by lyophilization. FIG. 2 shows the elution profile of the Sephadex G-75 column—3×200 cm. The column was eluted with 0.05M borate buffer of pH 8.0, 0.2M with respect to sodium chloride, and the eluates were collected in fractions of 24 ml. In the eluates, the specific trypsin inhibition was determined as described under 2.d., the specific inhibition of pig pancreatic elastase was determined as described under 2.a., and the inhibitor units—one IU (inhibitor unit) corresponds to the amount of inhibitor which inhibits 2 enzyme units by 50%—were ascertained. On the ordinate, the trypsin inhibition is given on the left—curve II- —and the elastase inhibition is given on the right-—curve I—in mIU/ml, and the fraction numbers are shown on the abscissa.

However, it is also possible to first adsorb the carbohydrate-containing inhibitors from the crude splitting mixture on a Concanavalin-A column in the manner already described, and, as has also already been described, to desorb the column with α-methylglycoside solution, after the contaminating substances have been washed out. The inhibitors contained in this desorbate can then be separated by gel filtration on molecular sieve columns in the manner which has already been described several times, the α-methylglycoside and, where relevant, salts in the solution being separated off at the same time.

According to the invention, the carbohydrate-free BI-8-E, called BI-8-E+ in the following text, can be obtained starting from the lyophilisate or from the solution, which is concentrated if necessary, by splitting off the carbohydrates with acid in a manner which is in itself known. It is particularly advantageous to use 60–90% formic acid at temperatures of 40°–70° C., preferably at 56° C.

However, it is also possible to use other acids, such as M sulphuric acid or M hydrochloric acid, at elevated temperatures between 50° and 100° C., preferably at 90° C. After neutralisation, the hydrolysis products and the acid are separated from the BI-8-E+ either by ultrafiltration using filters of defined pore size, such as for example, Amicon UM-2 membranes, or after concentration of the solution by gel filtration. Affinity carriers with antibodies, in particular monoclonal antibodies, can also be used to isolate the inhibitors according to the invention.

As already mentioned above, the elastase inhibitors BI-8-E and BI-8-E+ according to the invention have a leucine residue in the position $P_1$ of the peptide chain which is determining the specificity of the inhibitor. According to the results of the research groups of Powers and Zimmerman [M. Zimmerman and B. M. Ashe, Biochim. Biophys. Acta 480, 241 (1977); J. C. Powers, B. F. Gupton, A. D. Harley, N. Nishino and R. C. Whitley, Biochim. Biophys. Acta 485, 156 (1977); M. Castillo, K. Nakajima, M. Zimmerman and J. C. Powers, Analyt. Biochem. 99, 53 (1979) and K. Nakajima, J. C. Powers, B. M. Ashe and M. Zimmerman, J. Biol. Chem. 254, 4027 (1979)] obtained in investigations on the affinity of synthetic substrates and inhibitors for leucocyte elastase, pancreatic elastase, chymotrypsin and cathepsin G, the good inhibitory activity of the $Leu^{15}$ inhibitor for all these enzymes is surprising.

The inhibitors according to the invention have biological properties superior to BPTI. Their inhibitory actions on the elastases from the pancreas and leucocytes and on cathepsin G are of particular advantage and open up new possibilities of therapeutic use. Pancreatic elastase plays an important role in pancreatitis [M. C. Geokas, H. Rinderknecht, V. Swanson, B. P. Vitron and B. J. Haverback, Clin. Res. 16, 285 (1968)]; serum elastase plays an important role in atherosclerosis [U. Butturini and M. Langen, Klin. Wochenschr. 40, 472 (1962)] and leucocyte elastase plays an important role in acute and chronic inflammations with damage to connective tissue [A. Janoff, Amer. J. Pathol. 68, 579 (1972)], in damage to vessel walls [A. Janoff and J. D. Zeligs, Science 161, 702 (1968)] and in necrotizing diseases and degeneration of lung tissue, for example in cases of emphysema [G. M. Turino, R. M. Senior, B. D. Garg, S. Keller, M. M. Levi and I. Mandl, Science 165, 709 (1969); H. E. Evans, M. M. Levi and I. Mandl, Amer. Rev. Respir. Dis. 101, 359 (1970) and A. Janoff, R. A. Sandhaus, V. D. Hospelhorn and R. Rosenberg, Proc. Soc. Exptl. Biol. Med. 140, 516 (1972)]. The role of lysosomal enzymes, and especially of leucocyte elastase, in inflammatory reactions of immunological origin [M. Koono, M. Muto and H. Hayashi, Tohoku J. Exptl. Med. 94, 231 (1968)], for example rheumatoid arthritis [G. Weissmann and J. Spilberg, Arthritis Rheumat. 11, 162 (1968)] is equally important.

Another advantage of the inhibitors according to the invention is their low antigenicity and immunogenicity. Thus, although BI-14 reacts with anti-ITI antibodies, BI-8-E and BI-8-E+ do not.

The provision of the new inhibitors according to the invention thus represents an enrichment of pharmacy. The inhibitors according to the invention obtained from bovine serum are new. They can be characterized by chemical, physico-chemical, biochemical and biological properties and defined with respect to known substances. The following criteria were used:

1. Determination of the aminoacid sequence 300 mg of BI-8-E+ were reduced and the mercapto groups of the cysteine residues were carboxymethylated, as described by Crestfield and co-workers [A. M. Crestfield, S. Moore and W. H. Stein, J. Biol. Chem. 238, 622–627 (1963)]. After the excess reagents had been separated off by gel filtration on Bio-Gel P-2, aliquot portions of the inhibitor were enzymatically degraded with chymotrypsin and trypsin, in the latter case also after citraconylation in a manner which is in itself known [K. Hochstrasser and E. Wachter, H.S. Z. Physiol. Chem. 360, 1287–1296 (1979)]. The mixtures of substances thus obtained were separated into their components by ion exchange chromatography and gel chromatography as described by Hochstrasser and Wachter in the above investigation. The aminoacid sequences of the individual components were determined by Edman degradation in a solid phase sequentiator according to R. A. Laursen [R. A. Laursen, Europ. J. Biochem. 20, 80–91 (1971)].

By alignment of the corresponding partial sequences, the overall sequence of BI-8-R+ was determined: Lys-Ala-Asp-Ser-Cys-Gln-Leu-Asp-Tyr-Ser-Gln-Gly-Pro-Cys-Leu-Gly-Leu-Phe-Lys-Arg-Tyr-Phe-Tyr-Asn-Gly-Thr-Ser-Met-Ala-Cys-Glu-Thr-Phe-Leu-Tyr-Gly-Gly-Cys-Met-Gly-Asn-Leu-Asn-Asn-Phe-Leu-Ser-Gln-Lys-Glu-Cys-Leu-Glu-Thr-Cys-Arg.

2. Protease inhibition spectrum (a) Elastase inhibition (α) Pancreatic elastase inhibition Crystalline pancreatic elastase (pig) from Messrs. Nutritional Biochemical Corp. was used for the inhibiting experiments with the inhibitors according to the invention. Succinyl-L-alanyl-L-alanyl-L-alanine-p-nitroanilide [J. Bieth, B. Spiess and C. G. Wermuth, Biochem. Med. 11, 350 (1974)] was used as the substrate. Hydrolysis was monitored by continuous measurement of the extinction, at 405 nm, of the p-nitroaniline liberated. In order to ensure maximum complexing, the enzyme and inhibitor were pre-incubated for 15 minutes before addition of the substrate.

Figure 3:
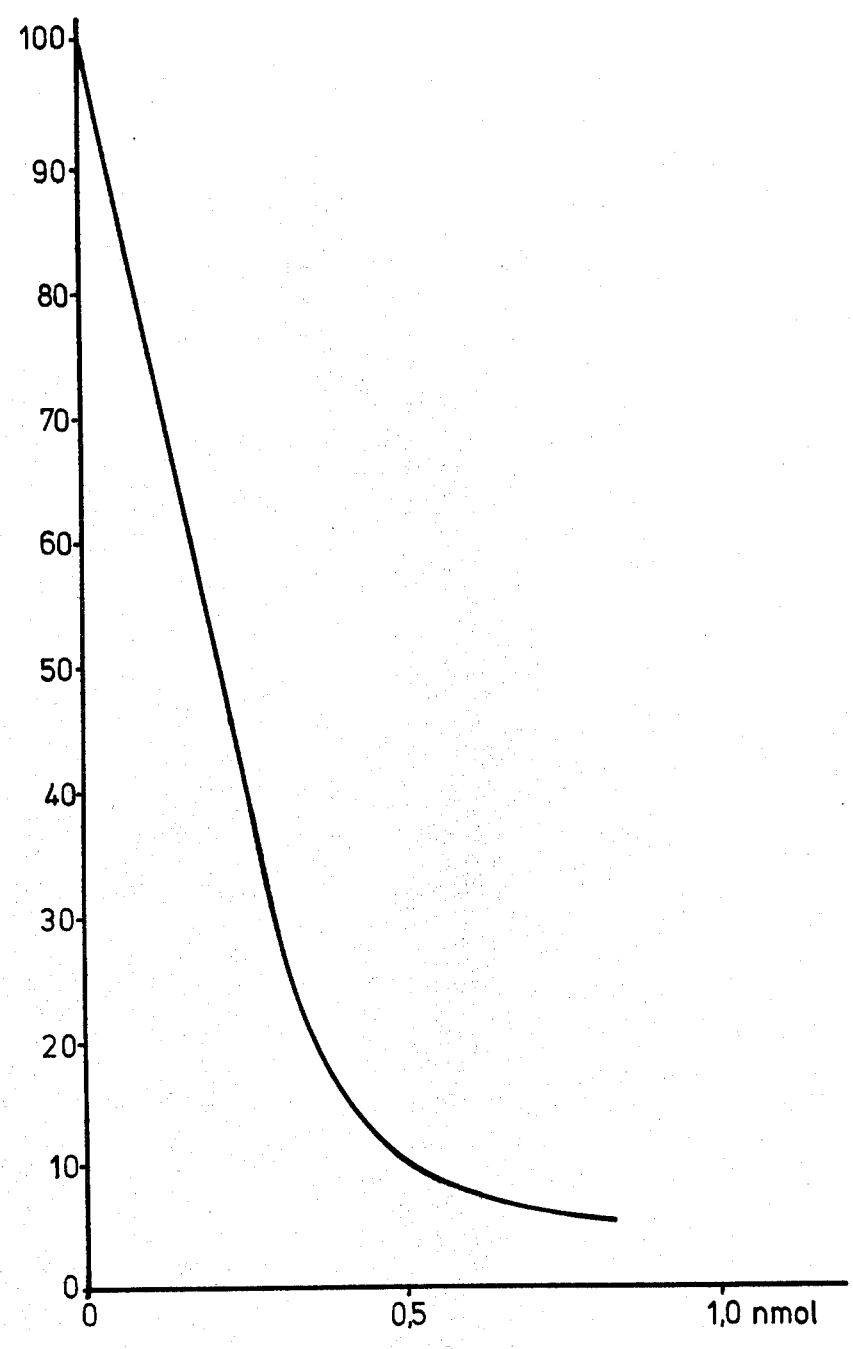

Semi-quantitative data relating to the inhibition of the enzyme for the inhibitors relevant in this case are summarized in Table 1. FIG. 3 shows the titration curve of pancreatic elastase (pig) with the BI-8-E according to the invention. The relative activity of the elastase is plotted on the ordinate and the amount of inhibitor (in nmols) is plotted on the abscissa.

(β) Leucocyte elastase inhibition

Succinyl-L-alanyl-L-alanyl-L-alanine-p-nitroanilide [J. Bieth, B. Spiess and C. G. Wermuth, Biochem. Med. 11, 350 (1974)] was used as the substrate. Data relating to the inhibition of leucocyte elastase for the inhibitors relevant in this case are shown in Table 1.

(b) Chymotrypsin inhibition

The activity of chymotrypsin was determined photometrically, with succinyl-L-phenylalanine-p-nitroanilide as the substrate, by the method of W. Nagel, F. Willig, W. Peschke and F. H. Schmidt, H.S. Z. Physiol. Chem. 340, 1 (1965), and the hydrolysis was determined by continuous measurement of the extinction, at 405 nm, of the p-nitroaniline liberated. The enzyme and inhibitor were preincubated in test buffer for 15 minutes before addition of the substrate.

Succinyl-L-phenylalanine-β-naphthyl ester was used as another substrate in the continuous test described by Schnabel [E. Schnabel, H.S. Z. Physiol. Chem. 362, 655–664 (1981)]. The enzyme and inhibitor were preincubated in test buffer at room temperature for 10–15 minutes before addition of the substrate.

Table 1 contains data relating to chymotrypsin inhibition for the inhibitors relevant in this case.

(c) Cathepsin G inhibition

The activity of cathepsin G was also determined with succinyl-L-phenylalanine-β-naphthyl ester by the method of E. Schnabel [H.S.Z. Physiol. Chem. 362, 655–664 (1981)].

Table 1 contains data relating to the inhibitory activity of the inhibitors relevant in this case.

(d) Trypsin inhibition

The trypsin activity was determined according to the method of H. Fritz, I. Trautschold and E. Werle [in Methoden der enzymatischen Analyse (Methods of Enzymatic Analysis), H. W. Bergmeyer ed., 2nd Edition, Volume 1, 1011 (1970)], with benzoyl-L-arginine-p-nitroanilide as the substrate. The p-nitroaniline liberated was monitored spectrophotometrically at 405 nm. The enzyme and inhibitor were pre-incubated for 15 minutes before addition of the substrate. Data relating to the inhibition of trypsin by the inhibitors relevant in this case are shown in Table 1.

It has furthermore been found that the inhibitors according to the invention have a prophylactic and also therapeutic action in models of acute inflammation. The inflammatory reactions are also significantly inhibited if the inhibitors are administered several hours after the inflammatory noxa has been set. This therapeutic action of the inhibitors results from their longer time of retention and thus action in the body of the experimental animals and their inhibition spectrum.

EXPERIMENTAL DESIGN FOR DEMONSTRATING THE ANTI-INFLAMMATORY ACTION IN RATS (a) Kaolin-induced inflammatory reaction The inflammatory reaction was induced by intraplantary injection of 0.1 ml of a 10% kaolin suspension into a hind paw of Wistar rats weighing 130–160 g. The inhibitors according to the invention used for the treatment of the inflammatory reaction were dissolved in 0.9% sodium chloride solution in a concentration of 10–20 mg/ml. The experimental animals were treated by intraperitoneal, intramuscular, subcutaneous or intravenous injection of 0.5–1.0 ml of the solution of the inhibitors, either *prophylactically*, that is to say *before* the inflammatory noxa had been set, or *therapeutically*, that is to say *after* the inflammatory noxa had been set. The swelling of the inflamed paw, which is a measure of the severity of the inflammatory reaction, was monitored with respect to time by a Kemper antiphlogmeter [F. Kemper and G. Ameln, Z.ges. exp. Med. 131, 407–411 (1959)].

The value measured 4 hours after the inflammatory noxa had been set was used to determine the dose/effect relationship.

Comparison of the action shows that the new inhibitors have an anti-inflammatory action superior to BPTI.

(b) Aerosil-induced inflammatory reaction

The inflammatory reaction was induced by intraplantary injection of 0.1 ml of a 2% Aerosil suspension into a hind paw of Wistar rats weighing 130–160 g. The inhibitors according to the invention used for the treatment of the inflammatory reaction were dissolved in 0.9% sodium chloride solution in a concentration of 10–20 mg/ml. The experimental animals were treated by intraperitoneal, subcutaneous or intravenous injection of 0.5–1.0 ml of the solution of the inhibitors 15 hours after the inflammatory noxa had been set. The swelling of the inflamed paw, which is a measure of the severity of the inflammatory reaction, was followed with respect to time using a Kemper antiphlogmeter. The 21 hour value after the induction of inflammation (=6 hours after injection of the inhibitors according to the invention) was determined to ascertain the dose/effect relationship.

The results of the therapeutic experiments with the new inhibitors according to the examples show the activity of the inhibitors used in this experimental model, in which the same dosage of BPTI does not inhibit the inflammatory reaction.

On the basis of their biological activity, the new inhibitors according to the invention prepared from bovine ITI can be used, in particular, for the treatment of the following diseases or symptoms:

1. various forms of shock, in particular shock lung and endotoxin shock, and post-traumatic and post-operative complications,
2. blood coagulation disorders,
3. acute and chronic inflammatory reactions, in particular for the therapy and prophylaxis of organ damage, such as, for example, pancreatitis and radiation-induced enteritis, inflammatory reactions caused by immune complexes, such as immunovasculitis, glomerulonephritis and arthritis; and collagenoses, in particular rheumatoid arthritis,
4. arthritis caused by deposits resulting from metabolism (for example gout),
5. degeneration of the elastic constituents of the connective tissue of organs, as in the case of atherosclerosis or pulmonary emphysema, and
6. radiation-induced enteritis.

The new active compounds can be converted into the customary formulations in a known manner (analogously to BPTI).

The following formulations are to be mentioned as preferred:

1. solutions for parenteral use for intravenous, intramuscular or subcutaneous injection or for intraarticular and intratumoral injection,
2. solutions for continuous intravenous infusion,
3. solutions for use as aerosols for inhalation, 4. solutions, emulsions, ointments, pastes, creams, lotions or powders for external local application, and 5. combinations with other inhibitors whose inhibition spectrums complement each other.

The concentrations of the new active compounds in the formulations according to the invention vary within the limits of 0.01 and 100 mg/ml of solution, preferably between 0.1 to 10 mg/ml of solution. Especially preferred are formulations containing 3.0 mg BPTI/ml physiological NaCl solution. In ointments, pastes and creames BPTI is present in a concentration of 0.1-10, preferably 1-5%. The new active compounds can be used in the customary manner, and the following methods of application are to be mentioned as particularly preferred:

(a) parenteral: intravenous, intramuscular, subcutaneous, intraarticular and intratumoral, (b) local: for example intranasal.

The following dose range may be given for the new active compounds according to the invention: 0.1-20 mg of active compound/kg of body weight, preferably 1 to 10 mg of active compound/kg of body weight; especially preferred one 1-3 mg/kg of body weight. The dose depends, above all, on the species to be treated and on the mode of administration.

The new active compounds according to the invention can be used on humans and animals.

EXAMPLE 1

(a) Isolation of physiological bovine ITI and separation of BI-8+.

428.6 g of 70% perchloric acid (257 ml) were stirred into 10 liters of bovine serum at room temperature, while mixing thoroughly, and the proteins precipitated were centrifuged off (40 minutes, 3,000 g) after the mixture had been left to stand for 2 hours. The sediment contains most of the natural and, where, relevant also the partially degraded ITI and was used, as described under (b), to obtain the polyvalent inhibitor with Mr 14,000.

The clear centrifugate was neutralized with 5N potassium hydroxide solution (about 600 ml) and the potassium perchlorate which had precipitated was separated off by filtration. The filtration residue was washed with water until the filtrate showed no absorption at 280 nm. The pH value of the solution was then adjusted to 7.8 with 2N potassium hydroxide solution, and trypsin-sepharose 4B was added, with slow mechanical stirring, until all the anti-tryptic activity (56 inhibitor units) was bonded. The trypsin-sepharose loaded with the trypsin inhibitors was isolated by filtering the suspension with suction using a glass sintered funnel. The filtration residue was washed with 500 ml of 0.2M triethanolamine/-hydrochloric acid buffer of pH 7.8, 0.2M in sodium chloride, and suspended in 250 ml of 0.2M potassium chloride/hydrochloric acid solution of pH 1.5. After the suspension had been left to stand at 20° C. for 2 hours, it was filtered over a column (5×30 cm), which was eluted with the potassium chloride/hydrochloric acid solution until the eluate no longer had any adsorption at 280 nm (total volume about 500 ml). The pH value of the eluates was adjusted to 7.8 by addition of sodium hydroxide solution and their volume was reduced to 25 ml by ultrafiltration using an Amicon UM-2 membrane. The retained material was filtered over Sephadex G-75, fine (column 3×200 cm) with 0.005M ammonium acetate buffer of pH 7.5 as the eluting agent.

The eluates were divided into three fractions according to their anti-tryptic activities:

1. physiological ITI (BI-30) with Mr 30,000 (about 5 inhibitor units; elution volume 450–600 ml)

2. modified ITI (BI-14) with Mr. 14,000 (about 20 inhibitor units; elution volume 600–795 ml)

3. serum inhibitor (BI-8+) with Mr 8,000 (about 25 inhibitor units; elution volume 795–975 ml)

(b) Isolation of the polyvalent tandem inhibitor BI-14

The perchloric acid precipitate isolated according to (a) was suspended in 7 liters of water. 5N potassium hydroxide solution was added to the suspension until a pH of 8.0 was reached, and the mixture was homogenized by stirring at 20° C. for 12 hours. The ITI fraction 1 from the Sephadex G-75 chromatography was then added to the suspension and the pH value of the mixture was readjusted to pH 8.0 with N sodium hydroxide solution. After the reaction mixture had been warmed to 37° C., 3 g of bovine trypsin were added. The mixture was stirred slowly and mechanically at 37° C. for 1 hour. 325 g of 70% perchloric acid (193 ml) were then added to the mixture, whilst stirring thoroughly, and the precipitate formed was separated off by centrifugation (40 minutes; 3,000 g) after the mixture had been left to stand at room temperature for 2 hours. The centrifugate was neutralised by addition of 5N potassium hydroxide solution and the potassium perchlorate which had precipitated was removed by filtration. The pH value of the filtrate was now brought to 7.8 with potassium hydroxide solution, and trypsin-sepharose was added in portions, whilst stirring slowly, until the total anti-tryptic activity of the solution (105 inhibitor units) had been bonded to the affinity carrier. The immobilised enzyme-inhibitor complex was isolated, as described under (a), by filtration with suction using a glass sintered funnel. A solution of the acid-stable trypsin inhibitors was obtained, as also described under (a), by filtration of the suspension of the trypsin-sepharose in 0.2M potassium chloride/hydrochloric acid solution of pH 1.5. After neutralization of this trypsin inhibitor solution with 5N sodium hydroxide solution, the solution was concentrated to about 50 ml by evaporation in vacuo and the concentrate was filtered over a Sephadex G-75 column (3×200 cm) with 0.01M ammonium acetate buffer as the eluting agent. The eluates containing the BI-14 (elution volume 600–800 ml corresponding to fraction 40–54 at a volume of 15 ml/fraction) were concentrated to a volume of 25 ml by ultrafiltration using an Amicon UM-2 membrane, and the salts were removed from this solution by filtration over a Bio-Gel P-2 column (5×50 cm) with water as the eluting agent, 2 protein peaks with elution volumes of 200–400 ml and 450–560 ml respectively being eluted; on eluting the column with a 0.2M potassium chloride solution adjusted to pH 1.5 with hydrochloric acid, a further peak was washed out, if the BI-8+ had not previously been removed by chromatography on Sephadex G 75, as described under (a). 100–110 mg of BI-14 were isolated from peak I by freeze-drying (50–55% of the anti-tryptic activity employed). Peak II and the potassium chloride eluate each contained 35 mg of an inhibitor which inhibits only trypsin (in each case 7% of the anti-tryptic activity employed). The inhibition profile of BI-14 can be seen from Table 1.

(c) Isolation of the elastase inhibitor BI-8-E 200 mg (14.3 μmols) of BI-14 obtained according to (b) were dissolved in 75 ml of 0.2M triethanolamine/hydrochloric acid buffer of pH 7.8 and the solution was incubated with 800 mg of trypsin (30 μmols), dissolved in the same buffer at 37° C. for 2 hours. 7.5 ml of 70% perchloric acid were then added to the solution and the precipitate was separated off by centrifugation (30 minutes, 5,000 g), after the mixture had been left to stand for 6 hours. The centrifugate was neutralized with 5N potassium hydroxide solution (18 ml) and the potassium perchlorate which had precipitated was separated off by filtration. The filtrate was concentrated to a volume of 20 ml by ultrafiltration using an Amicon UM-2 membrane. The concentrate was put onto a 3×200 cm Sephadex G-75 column and the column was eluted with 0.05M sodium borate buffer of pH 8.0, containing 0.2M sodium chloride. The anti-tryptic and the elastase inhibitory activity in the eluates were determined. The result of this chromatography is shown in FIG. 1. The BI-8-T coeluting with BI-8-E was separated off in a manner which has already been described several times, by direct filtration of the solution over a 3×15 cm trypsin-sepharose column. The eluates containing the BI-8-E were concentrated to a volume of 20 ml by ultrafiltration using an Amicon UM-2 membrane, and the salts were then removed from this solution by filtration over a Bio-Gel P-2 column—1.5×150 cm—equilibrated with a 1M ammonium acetate solution. The fractions containing the inhibitor were combined and the BI-8-E was isolated by freeze-drying. 15 mg (~15%) of colourless BI-8-E were thereby obtained. Data relating to the inhibiting behaviour of this inhibitor are contained in Table 1.

(d) BI-8-E+

10 mg of BI-8-E obtained according to (c) were dissolved in 2 ml of 80% formic acid. This solution was kept at 56° C. for 12 hours. The solution was then filtered over a Bio-Gel P-2 column (1.5×100 cm) using water as the eluting agent. The protein-containing eluates were combined and lyophilized. 4.5–6.5 mg of a colourless substance with 50–80% of the elastase-inhibitory activity employed were thereby obtained. The inhibition spectrum of the carbohydrate-free BI-8-E+ according to the invention can be seen from Table 1.

EXAMPLE 2

Perchloric acid precipitate obtained from 10 liters of bovine serum as described in Example 1.a was made into a paste with 7 liters of water. After 5N sodium hydroxide solution had been added until the pH was 8.2, the mixture was homogenized by stirring at 20° C. for 12 hours. 3.5 g of trypsin were added to the suspension and the mixture was kept at 37° C. for 18 hours, whilst stirring slowly. 325 g of 70% perchloric acid (195 ml) were then added to the mixture and, after the mixture had been left to stand at 20° C. for 2 hours, the precipitate was separated off by centrifugation (40 minutes; 3,000 g). The pH value of the centrifugate was adjusted to 7.8 with 5N potassium hydroxide solution. The potassium perchlorate which had precipitated was separated off by filtration. The trypsin inhibitors present in the filtrate were complexed by adding trypsin-sepharose 4B in portions, and the insoluble enzyme-inhibitor complexes were separated off by filtration. The volume of the filtrate was reduced to about 700 ml in vacuo, and the filtrate was filtered over a column (2.5×20 cm) filled with Concanavalin-A-sepharose and equilibrated with 0.05M tris-hydrochloric acid buffer of pH 8.0, using the equilibrating buffer as the eluting agent. The elastase inhibitor BI-8 according to the invention and the modified BI-14+ were eluted with 0.05M sodium acetate buffer of pH 6.0, 0.05M relative to 60-methylmannoside. The salts were removed from the inhibitor-containing eluates by ultrafiltration using an Amicon UM-2 membrane.

The BI-14+ and BI-8-E were separated by gel filtration on Sephadex G-75, as described in Example 1.c. After removal of the salts over Bio-Gel P-2 and freeze drying 10 mg of BI-8-E were obtained.

EXAMPLE 3

200 mg of BI-14 obtained according to Example 1.b. were dissolved in 75 ml of 0.2M triethanolamine/hydrochloric acid buffer of pH 7.8, and hydrolysis with 800 mg of trypsin and working up were carried out as described in Example 1.c). As described in Example 1.a, trypsin-sepharose 4B was added to the solution of the inhibitors which was obtained after the potassium perchlorate had been removed, until the total anti-tryptic activity of the solution was bonded to the trypsin. The charged trypsin-sepharose was then separated off by filtration over a glass sintered funnel (D2) and eluted thoroughly with a total of 200 ml of 0.2M triethanolamine/hydrochloric acid buffer of pH 7.8, 0.2M relative to sodium chloride. The filtrate and washing water were combined, and chymotrypsin-sepharose 4B was added until no further elastase inhibition could be detected in the supernatant. The chymotrypsin-sepharose charged with the BI-14+ and the BI-8-E was transferred to a 2.5×30 cm column and washed with the above triethanolamine/hydrochloric acid buffer.

For desorption of the elastase inhibitors BI-14+ and BI-8-E, the column was eluted with 250 ml of a 0.2M potassium chloride/hydrochloric acid solution of pH 1.5, after being eluted with water, until the eluates had no absorbance at 280 nm. The eluates with inhibitory activity for elastase were pooled and, after neutralization with N potassium hydroxide solution, the volume of the solution thus obtained was reduced to about 10 ml by ultrafiltration using an Amicon UM-2 membrane.

To separate BI-14+ from the residual salts, the concentrate was filtered over a column—3×200 cm—filled with Sephadex G-75.

0.1M ammonium acetate solution of pH 7.5 served as the eluting agent.

The eluates were collected in fractions of 24 ml and their inhibitory action on elastase was determined. The elution profile of the column can be seen from FIG. 1. The eluates containing the BI-8-E were pooled and the inhibitor was isolated by freeze-drying. 10–20 mg of colourless lyophilisate were obtained. BI-8-E+ can be prepared from the BI-8-E as described in Example 1.d.

EXAMPLE 4

For parenteral injection: 800 mg BI-8-E obtained according to example 1, 2 or 3 were dissolved in 200 ml of physiological saline. The solution was filtered through a membrane filter for sterilization and was tyndallized. The thus treated filtrate was bottled in sterilized glass ampoules in portions of 5, 10 or 50 ml. These ampoules were sealed and are ready for use.

EXAMPLE 5

Lyophilized injection: 800 mg BI-8-E obtained according to example 1, 2 or 3 were dissolved and processed as described in example 4. The ampoules were lyophilized prior to sealing.

TABLE 1

| | Inhibition spectra of the inhibitors obtained from bovine III | | | | |
|---|---|---|---|---|---|
| | ENZYME | | | | |
| INHIBITOR | α-Chymotrypsin (bovine) | Granulocyte elastase (human) | Pancreas elastase (pig) | Cathepsin G (human) | Trypsin (bovine) |
| BI-14 | ++++ | +++ | +++ | ++ | +++ |
| BI-14+ | +++ | +++ | +++ | ++ | (+) |
| BI-8-E (according to the invention) | +++ | +++ | +++ | ++ | − |
| BI-8-E+ (according to the invention) | +++ | +++ | +++ | ++ | − |
| BI-8-T | ++ | − | − | ++ | +++ |

What is claimed is:

1. An elastase inhibitor of the formula I $$\text{Lys—Ala—Asp—Ser—Cys—Gln—Leu—Asp—Tyr—Ser—}$$
$$\text{—Gln—Gly—}$$
$$\text{Pro—Cys—Leu—Gly—Leu—Phe—Lys—Arg—Tyr—Phe—}$$
$$\text{—Tyr—}$$
$$\overset{X}{|}$$
$$\text{Asn—Gly—Thr—Ser—Met—Ala—Cys—Glu—Thr—Phe—}$$
$$\text{—Leu—Tyr—Gly—}$$
$$\text{Gly—Cys—Met—Gly—Asn—Leu—Asn—Phe—Leu—}$$
$$\text{—Ser—Gln—Lys—}$$
$$\text{Glu—Cys—Leu—Glu—Thr—Cys—Arg,}$$

(I)

in which

X represents hydrogen or a glycoside residue built-up from residues of N-acetylneuraminic acid, N-acetylglucosamine, glactose and mannose.

2. An elastase inhibitor of the formula (I) in claim 1, in which X denotes a glycoside residue (BI-8-E).

3. An elastase inhibitor of the formula (I) in claim 1, in which X denotes hydrogen (BI-8-E+).

4. A pharmaceutical composition containing as an active ingredient, an amount effective for combatting acute or chronic inflammatory reaction of an elastase inhibiting peptide of claim 1 in admixture with an inert pharmaceutical carrier.

5. A pharmaceutical composition of claim 4 in the form of a sterile or physiologically isotonic aqueous solution.

6. A composition according to claim 4 containing from 0.5 to 90% by weight of the said active ingredient.

7. A medicament in dosage unit form comprising an elastase inhibiting peptide according to claim 1 and an inert pharmaceutical carrier.

8. A medicament of claim 7 in the form of tablets, pills, dragees, capsules, ampoules or suppositories.

9. A process for treating acute or chronic inflammation in warm-blooded animals which comprises administering to the animals an amount effective for treatment of acute or chronic inflammation of a peptide of claim 1 either alone or in admixture with an inert pharmaceutical carrier or in the form of a medicament.

* * * * *

UNITED STATES PATENT AND TRADEMARK OFFICE
CERTIFICATE OF CORRECTION

PATENT NO. :   4,485,100
DATED      :   November 27, 1984
INVENTOR(S) :  Karl Hochstrasser, et al It is certified that error appears in the above-identified patent and that said Letters Patent is hereby corrected as shown below:

Col. 12, line 6            Delete "60" and substitute -- $\alpha$ --

Col. 13, line 41          After "Asn" insert --Asn--

Signed and Sealed this

Sixteenth Day of April 1985

[SEAL]

*Attest:*

DONALD J. QUIGG

*Attesting Officer*      *Acting Commissioner of Patents and Trademarks*